(12) United States Patent
Hofstetter et al.

(10) Patent No.: US 11,869,381 B2
(45) Date of Patent: *Jan. 9, 2024

(54) HYSTERECTOMY MODEL

(71) Applicant: Applied Medical Resources Corporation, Rancho Santa Margarita, CA (US)

(72) Inventors: Gregory K. Hofstetter, Rancho Santa Margarita, CA (US); Anysa Fernandez, Chino, CA (US)

(73) Assignee: Applied Medical Resources Corporation

( * ) Notice: Subject to any disclaimer, the term of this patent is extended or adjusted under 35 U.S.C. 154(b) by 63 days.

This patent is subject to a terminal disclaimer.

(21) Appl. No.: 17/695,644

(22) Filed: Mar. 15, 2022

(65) Prior Publication Data
US 2022/0208025 A1 Jun. 30, 2022

Related U.S. Application Data

(63) Continuation of application No. 16/190,430, filed on Nov. 14, 2018, now Pat. No. 11,276,330.
(Continued)

(51) Int. Cl.
*G09B 23/24* (2006.01)
*G09B 23/34* (2006.01)
(Continued)

(52) U.S. Cl.
CPC ............... *G09B 23/34* (2013.01); *G09B 9/00* (2013.01); *G09B 23/281* (2013.01);
(Continued)

(58) Field of Classification Search
CPC ........ G09B 23/34; G09B 9/00; G09B 23/281; G09B 23/285; G09B 23/32; A61B 17/42; A61B 2017/00716; A61B 2017/4216
See application file for complete search history.

(56) References Cited

U.S. PATENT DOCUMENTS 2,495,568 A 1/1950 Coel
7,866,983 B2 1/2011 Hemphill et al.
(Continued)

FOREIGN PATENT DOCUMENTS

WO WO 2015/139690 A1 9/2015
WO WO 2017/059417 A1 4/2017
WO WO 2017/087746 A1 5/2017

OTHER PUBLICATIONS

European Patent Office, The International Search Report and Written Opinion for International Application No. PCT/US2018/060926, entitled "Hysterectomy Model," dated Jan. 29, 2019, 13 pgs.
(Continued)

*Primary Examiner* — Robert P Bullington
(74) *Attorney, Agent, or Firm* — Thomas Nguyen; Patrick Ikehara

(57) ABSTRACT

A surgical simulator for surgical training is provided. The simulator includes a frame defining an enclosure and a simulated tissue model located inside the frame. The simulated tissue model is adapted for practicing a number of surgical procedures including but not limited to transanal excisions and transvaginal hysterectomies. Portions of the frame comprises a material adhesively compatible with the material of portions of the simulated tissue model to secure and suspend the simulated tissue model within the frame. The simulated tissue model may also include simulated vasculature configured to loop through apertures in the frame to secure and suspend the simulated tissue model within the frame.

19 Claims, 7 Drawing Sheets

Related U.S. Application Data

(60) Provisional application No. 62/586,059, filed on Nov. 14, 2017.

(51) Int. Cl.
    *G09B 23/32*     (2006.01)
    *G09B 9/00*     (2006.01)
    *G09B 23/28*     (2006.01)
    *A61B 17/42*     (2006.01)
    *A61B 17/00*     (2006.01)

(52) U.S. Cl.
    CPC ........... *G09B 23/285* (2013.01); *G09B 23/32* (2013.01); *A61B 17/42* (2013.01); *A61B 2017/00716* (2013.01); *A61B 2017/4216* (2013.01)

(56) References Cited

U.S. PATENT DOCUMENTS

| | | |
|---|---|---|
| 7,931,471 B2 | 4/2011 | Senagore et al. |
| 8,708,707 B2 | 4/2014 | Hendrickson et al. |
| 8,968,003 B2 | 3/2015 | Hendrickson et al. |
| 9,123,261 B2 | 9/2015 | Lowe |
| 9,373,270 B2 | 6/2016 | Miyazaki |
| 9,472,123 B2 | 10/2016 | Trotta et al. |
| 9,830,834 B2 | 11/2017 | Miyazaki |
| 9,997,088 B2 | 6/2018 | Miyazaki |
| 2014/0087347 A1 | 3/2014 | Tracy et al. |
| 2015/0371560 A1 | 12/2015 | Lowe |
| 2016/0260358 A1 | 9/2016 | Miyazaki |
| 2016/0365007 A1 | 12/2016 | Black et al. |
| 2017/0011657 A1 | 1/2017 | Chanda et al. |
| 2017/0039892 A1 | 2/2017 | Simoes et al. |
| 2017/0046984 A1 | 2/2017 | Robertson |
| 2017/0069231 A1 | 3/2017 | Trotta et al. |
| 2017/0148356 A1 | 5/2017 | Black et al. |
| 2017/0301263 A1 | 10/2017 | Souter et al. |
| 2018/0005549 A1 | 1/2018 | Black et al. |
| 2018/0075777 A1 | 3/2018 | Iverson et al. |
| 2019/0147769 A1* | 5/2019 | Hofstetter .............. G09B 23/34 434/273 |

OTHER PUBLICATIONS

The International Bureau of WIPO, International Preliminary Report on Patentability for International Application No. PCT/US2018/060926, entitled "Hysterectomy Model," dated May 28, 2020, 8 pgs.

* cited by examiner

HYSTERECTOMY MODEL

CROSS-REFERENCE TO RELATED APPLICATIONS

This application is a continuation of U.S. patent application Ser. No. 16/190,430, filed Nov. 14, 2018, which claims the benefit of U.S. Provisional Patent Application Ser. No. 62/586,059, filed on Nov. 14, 2017, the disclosure of which is hereby incorporated by reference in its entirety.

BACKGROUND

This application is generally related to surgical training tools, and in particular, to simulated tissue structures and models for teaching and practicing various surgical techniques and procedures related but not limited to laparoscopic, endoscopic and minimally invasive surgery.

Medical students as well as experienced doctors learning new surgical techniques must undergo extensive training before they are qualified to perform surgery on human patients. The training must teach proper techniques employing various medical devices for cutting, penetrating, clamping, grasping, stapling, cauterizing and suturing a variety of tissue types. The range of possibilities that a trainee may encounter is great. For example, different organs and patient anatomies and diseases are presented. The thickness and consistency of the various tissue layers will also vary from one part of the body to the next and from one patient to another. Different procedures demand different skills. Furthermore, the trainee must practice techniques in various anatomical environs that are influenced by factors such as the size and condition of the patient, the adjacent anatomical landscape and the types of targeted tissues and whether they are readily accessible or relatively inaccessible.

Numerous teaching aids, trainers, simulators and model organs are available for one or more aspects of surgical training. However, there is a need for models or simulated tissue elements that are likely to be encountered in and that can be used for practicing endoscopic and laparoscopic, minimally invasive, transluminal surgical procedures. In laparoscopic surgery, a trocar or cannula is inserted to access a body cavity and to create a channel for the insertion of a camera such as a laparoscope. The camera provides a live video feed capturing images that are then displayed to the surgeon on one or more monitors. At least one additional small incision is made through which another trocar/cannula is inserted to create a pathway through which surgical instruments can be passed for performing procedures observed on the monitor. The targeted tissue location such as the abdomen is typically enlarged by delivering carbon dioxide gas to insufflate the body cavity and create a working space large enough to accommodate the scope and instruments used by the surgeon. The insufflation pressure in the tissue cavity is maintained by using specialized trocars. Laparoscopic surgery offers a number of advantages when compared with an open procedure. These advantages include reduced pain, reduced blood and shorter recovery times due to smaller incisions.

Laparoscopic or endoscopic minimally invasive surgery requires an increased level of skill compared to open surgery because the target tissue is not directly observed by the clinician. The target tissue is observed on monitors displaying a portion of the surgical site that is accessed through a small opening. Therefore, clinicians need to practice visually determining tissue planes, three-dimensional depth perception on a two-dimensional viewing screen, hand-to-hand transfer of instruments, suturing, precision cutting and tissue and instrument manipulation. Typically, models simulating a particular anatomy or procedure are placed in a simulated pelvic trainer where the anatomical model is obscured from direct visualization by the practitioner. Ports in the trainer are employed for passing instruments to practice techniques on the anatomical model hidden from direct visualization. Simulated pelvic trainers provide a functional, inexpensive and practical means to train surgeons and residents the basic skills and typical techniques used in laparoscopic surgery such as grasping, manipulating, cutting, tying knots, suturing, stapling, cauterizing as well as how to perform specific surgical procedures that utilized these basic skills. Simulated pelvic trainers are also effective sales tools for demonstrating medical devices required to perform these laparoscopic procedures.

One procedure is a hysterectomy in which the uterus is removed. The hysterectomy may be performed vaginally extracting the uterus through the vaginal canal or abdominally through a small incision in the abdomen. The vaginal hysterectomy is historically hard to train on as the field of view is limited. Unlike laparoscopic procedures, there is no camera that is projecting the surgery onto a screen and unlike open procedures there is not a wide incision that can be viewed by multiple people. As such, the best way to teach a vaginal hysterectomy is through a simulated model. Therefore, there is a need for model for training hysterectomy procedures.

SUMMARY

In accordance with various embodiments of the present invention a surgical simulator is provided. The surgical simulator comprises a frame comprising a base and a top cover defining a lumen extending along a longitudinal axis of the frame, the lumen having at least one of a proximal opening and a distal opening, the top cover connected to the base and the base covered with a first material. The surgical simulator further comprising at least one artificial tissue structure connected and suspended within the lumen and the at least one artificial tissue structure having a bottom portion being made of a second material and in direct contact with the first material of the base.

In accordance with various embodiments, a surgical simulator comprises a frame and at least one artificial tissue structure. The frame comprises a base, an upper wall and two sidewalls. The frame defines a lumen extending along a longitudinal axis of the frame and the lumen has at least one of a proximal opening and a distal opening. The at least one of the two sidewalls has a plurality of apertures. The at least one artificial tissue structure is connected and suspended within the lumen and the at least one artificial tissue structure comprises a plurality of simulated vasculature. The at least one of the plurality of simulated vasculature has a free end extending through a first aperture of the plurality of apertures and out through a second aperture next to the first aperture.

In accordance with various embodiments, a surgical simulator for surgical training comprise a frame comprising a base, an upper wall and two sidewalls. The frame defines a lumen extending along a longitudinal axis of the frame and the lumen has at least one of a proximal opening and a distal opening. The surgical simulator further comprises an artificial uterus, an artificial vaginal canal defining an opening at the proximal end and connected to the artificial uterus at the distal end, an artificial rectum having a lumen defining a proximal opening, an artificial bladder; and a silicone sheet having a top surface and a bottom surface. In various embodiments, the artificial uterus and the artificial bladder are connected to the bottom surface of the silicone sheet and the artificial vaginal canal and the artificial rectum are connected to the top surface of the silicone sheet.

These and other features of the present invention will become more apparent with a discussion of embodiments in reference to the associated drawings.

BRIEF DESCRIPTION OF THE DRAWINGS

The present inventions may be understood by reference to the following description, taken in connection with the accompanying drawings in which the reference numerals designate like parts throughout the figures thereof.

DETAILED DESCRIPTION

Figure 1:
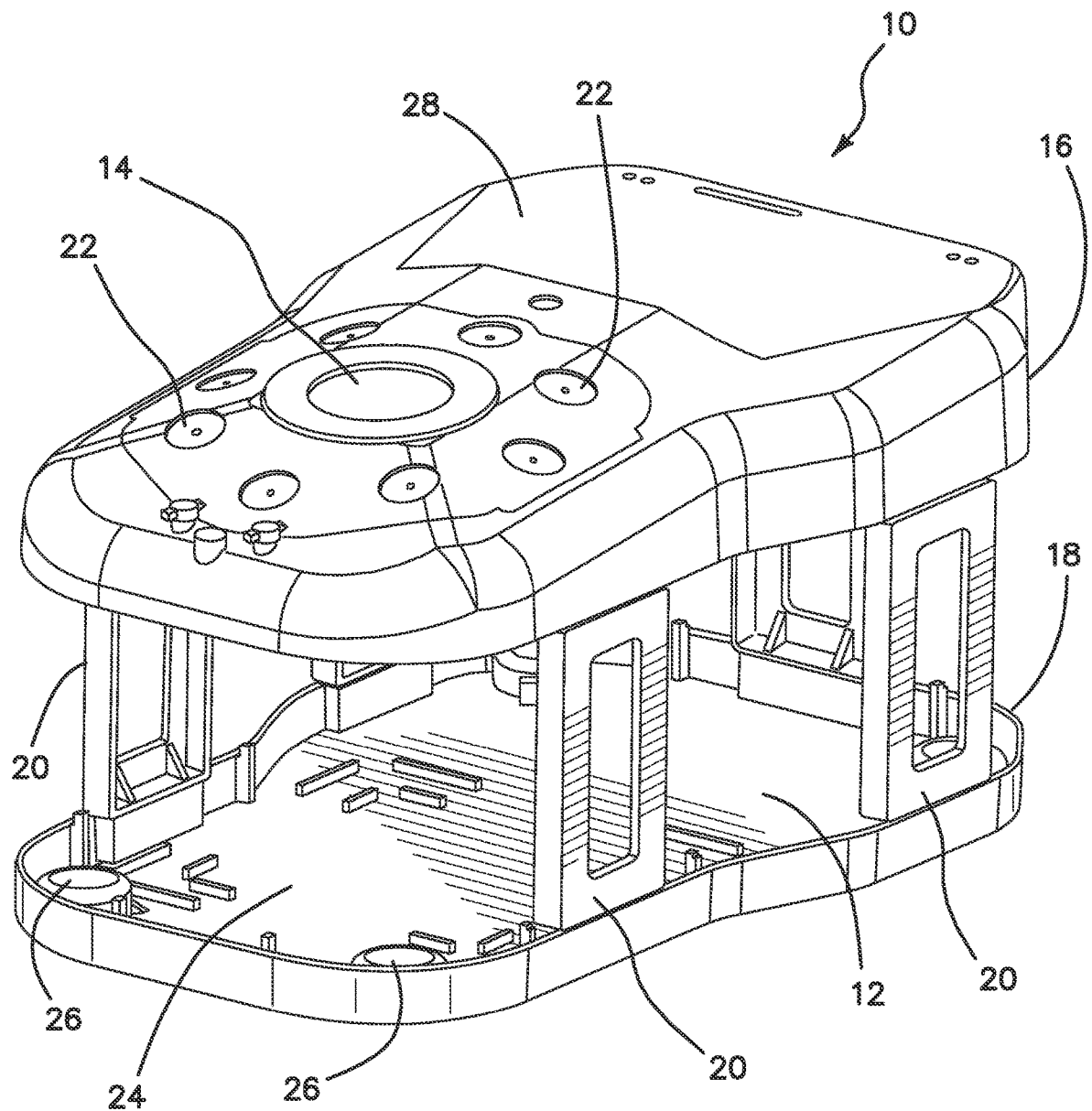
FIG. 1 is a top perspective view of a surgical training device according to various embodiments of the present invention.
Figure 2:
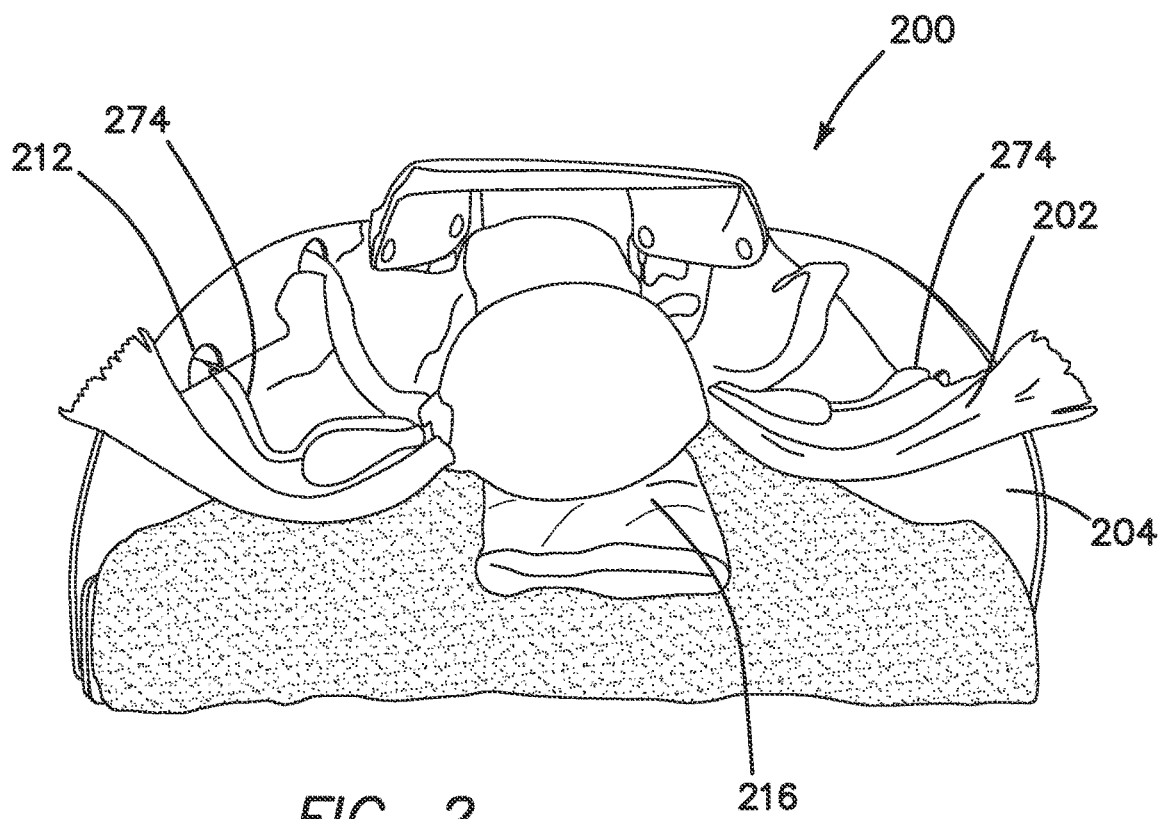
FIG. 2 is a back perspective view of a surgical simulator or model according to various embodiments of the present invention.

A surgical training device 10 that is configured to mimic the torso of a patient such as the abdominal region is shown in FIG. 1. The surgical training device 10 provides a body cavity 12 substantially obscured from the user for receiving simulated or live tissue or model organs or training models of the like described in this invention. The body cavity 12 is accessed via a tissue simulation region 14 that is penetrated by the user employing devices to practice surgical techniques on the tissue or practice model found located in the body cavity 12. Although the body cavity 12 is shown to be accessible through a tissue simulation region, a hand-assisted access device or single-site port device may be alternatively employed to access the body cavity 12. An exemplary surgical training device is described in U.S. patent application Ser. No. 13/248,449 entitled "Portable Laparoscopic Trainer" filed on Sep. 29, 2011 and incorporated herein by reference in its entirety. The surgical training device 10 is particularly well suited for practicing laparoscopic or other minimally invasive surgical procedures.

Still referencing FIG. 1, the surgical training device 10 includes a top cover 16 connected to and spaced apart from a base 18 by at least one leg 20. FIG. 1 shows a plurality of legs 20. The surgical training device 10 is configured to mimic the torso of a patient such as the abdominal region. The top cover 16 is representative of the anterior surface of the patient and the space 12 between the top cover 16 and the base 18 is representative of an interior of the patient or body cavity where organs reside. The surgical trainer 10 is a useful tool for teaching, practicing and demonstrating various surgical procedures and their related instruments in simulation of a patient undergoing a surgical procedure. Surgical instruments are inserted into the cavity 12 through the tissue simulation region 14 as well as through pre-established apertures 22 in the top cover 16. Various tools and techniques may be used to penetrate the top cover 16 to perform mock procedures on simulated organs or practice models placed between the top cover 16 and the base 18. The base 18 includes a model-receiving area 24 or tray for staging or holding a simulated tissue model or live tissue. The model-receiving area 24 of the base 18 includes frame-like elements for holding the model (not shown) in place. To help retain a simulated tissue model or live organs on the base 18, a clip attached to a retractable wire is provided at locations 26. The retractable wire is extended and then clipped to hold the tissue model in position substantially beneath the tissue simulation region 14. Other means for retaining the tissue model include a patch of hook-and-loop type fastening material (VELCRO®) affixed to the base 18 in the model receiving area 24 such that it is removably connectable to a complementary piece of hook-and-loop type fastening material (VELCRO®) affixed to the model.

A video display monitor 28 that is hinged to the top cover 16 is shown in a closed orientation in FIG. 1. The video monitor 28 is connectable to a variety of visual systems for delivering an image to the monitor. For example, a laparoscope inserted through one of the pre-established apertures 22 or a webcam located in the cavity and used to observe the simulated procedure can be connected to the video monitor 28 and/or a mobile computing device to provide an image to the user. Also, audio recording or delivery means may also be provided and integrated with the trainer 10 to provide audio and visual capabilities. Means for connecting a portable memory storage device such as a flash drive, smart phone, digital audio or video player, or other digital mobile device is also provided, to record training procedures and/or play back pre-recorded videos on the monitor for demonstration purposes. Of course, connection means for providing an audio visual output to a screen larger than the monitor is provided. In another variation, the top cover 10 does not include a video display but includes means for connecting with a laptop computer, a mobile digital device or tablet and connecting it by wire or wirelessly to the trainer.

When assembled, the top cover 16 is positioned directly above the base 18 with the legs 20 located substantially around the periphery and interconnected between the top cover 16 and base 18. The top cover 16 and base 18 are substantially the same shape and size and have substantially the same peripheral outline. The internal cavity is partially or entirely obscured from view. In the variation shown in FIG. 1, the legs include openings to allow ambient light to illuminate the internal cavity as much as possible and also to advantageously provide as much weight reduction as possible for convenient portability. The top cover 16 is removable from the legs 20 which in turn are removable or collapsible via hinges or the like with respect to the base 18. Therefore, the unassembled trainer 10 has a reduced height that makes for easier portability. In essence, the surgical trainer 10 provides a simulated body cavity 12 that is obscured from the user. The body cavity 12 is configured to receive at least one surgical model accessible via at least one tissue simulation region 14 and/or apertures 22 in the top cover 16 through which the user may access the models to practice laparoscopic or endoscopic minimally invasive surgical techniques.

Figure 6:
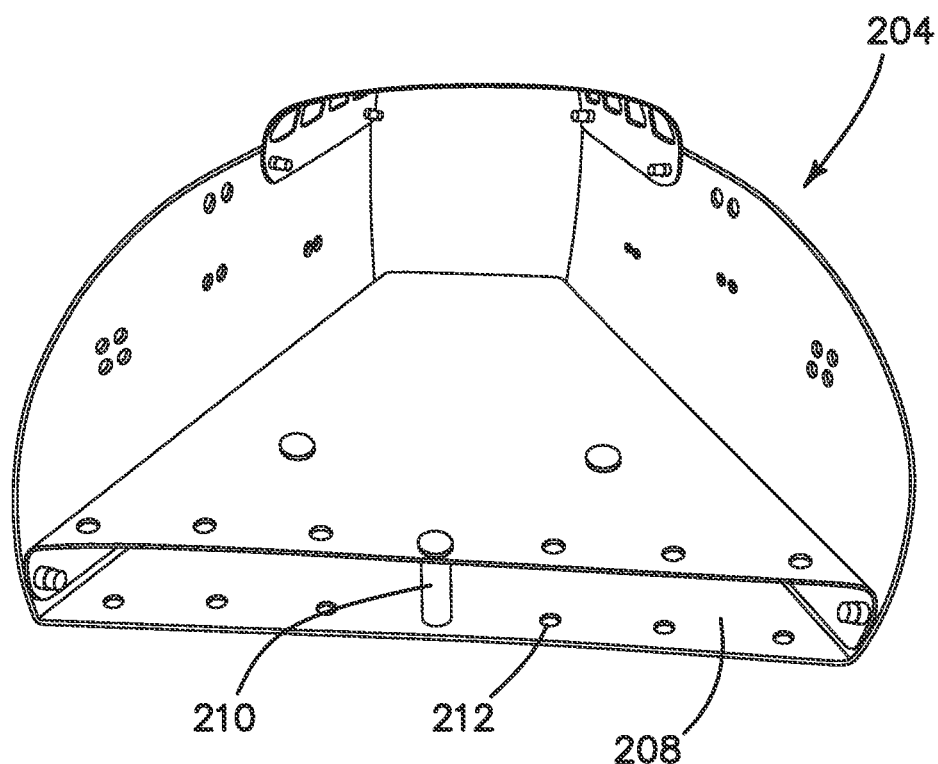
FIG. 6 is a back perspective view of a frame according to various embodiments of the present invention.

Turning now to FIGS. 2-7, a hysterectomy model 200 is shown. The model 200 includes a plurality of simulated organ structures 202 connected to and located inside a frame 204. The frame 204 is configured to simulate a pelvis and serve as a box-like encasement for housing the plurality of simulated organ structures 202. The frame 204 comprises two or more pieces of semi-rigid plastic. The frame 204 includes a top frame portion 206 connected with fasteners 210 to a side frame or bottom frame portion 208 to form a top planar surface and a bottom planar surface interconnected by two upstanding sidewalls. The top planar surface and the bottom planar surface are parallel with each other and form corners with the sidewalls from which the sidewalls bow outwardly as seen in FIG. 6. The assembled frame 204 having a base and a top interconnected by two upstanding sidewalls defines a central lumen with an open proximal end and an open distal end. The area of the central lumen in cross-section taken perpendicular to the longitudinal axis increases progressively with increasing distance from the proximal end toward the distal end. The outer shape of the frame 204 can be dissimilar from the shape of the central lumen. The sidewalls are angled towards each other such that at the proximal end the distance between the sidewalls is close and increases progressively with increasing distance toward the distal end where the sidewalls are farther apart from each other. In various embodiments, the frame is tapered having a frusto-conical shape such that it has a central lumen with increasing area that does not have corners. The outer shape of the frame may also match the tapered shape of the central lumen. The frame 204 has a flat base, permitting it to be placed and stood on a flat surface.

In various embodiments, the bottom frame portion 208 includes a first level and a raised second floor 209 that raises the level of the model inside the frame 204 to be in line with a transvaginal adapter (not shown) that in various embodiments is used to connect the model to a laparoscopic trainer 10. The frame 204 may include apertures 212 for passing of fasteners 210 and/or connecting tissue structures, such as vasculature 274, by passing them through and looping around the apertures and suspending them in the frame 204. The frame 204 is comprised of folded plastic that is transparent and/or translucent. The folding of the plastic components of the frame 204 results in corners that are representative of a pelvis that is not anatomically correct yet provides advantages needed in simulating laparoscopic procedures in exchange for the realism of an anatomically correct pelvis. These advantages include the mechanical constriction of organs located in the tapered proximal end having the smallest luminal cross-sectional area. The physical constriction of organs at the proximal end creates a more rigid response in the organs when manipulated by surgical instruments relative to the distal end where organs located therein are less constricted and freer to pendulate and more fluidly respond to manipulations with surgical instruments. The frame 204 in accordance with various embodiments is an intentional simplification of the pelvis that combines variable resistance in the organs along the length of the longitudinal axis of the central lumen. The smaller opening to the central lumen at the proximal end of the frame is where the opening to the vaginal canal would be positioned when the organs are placed inside the frame. The proximal end of the frame is also oriented toward a transvaginal or transanal adapter for connection therewith. The distal end of the frame 204 is the location of the artificial uterus 216. The central lumen of the frame expands, widens and angles outwardly towards the distal end. This taper of the box-like frame widens relaxing the organs located therein and the narrow proximal end constricts the organs, limiting the range of motion of the organs relatively more as a result of supporting the organs in closer confines.

The frame 204 is generally comprised of two or more structures. These structures may include some variation of a top, right side wall, left side wall and bottom platform, all made of one or more components. The base structures can be assembled utilizing various fasteners and/or adhesive. The top and side walls create a constricted work area which is beneficial to the end user; however, can pose difficulty in manufacturing. Utilizing a top that is independent of the side walls allows for ease of assembly during the manufacturing process. The organ model can be placed atop the bottom frame portion 208 or, if employed, atop a raised second floor 209 for assembly and the top can be fastened once the assembly is complete. Moreover, any frame component which is not permanently adhered to any other material can be reused by manufacturers and/or the end user. Thus, a frame comprised of two or more structures encourages salvage and reuse of the frame components which are not damaged during manufacturing and/or use. Due to ease of disassembly, frame components can also be removed by the end user to make adjustments to the organ structures connected thereto as needed, or to remove one or more organ structures for assessment after the user has completed simulated procedural training on the organ structures. In various embodiments, the frame 204 is made from five components or structures including a top or top portion 211, two sidewalls and two bottom components 208, 209 that interlock to create a frame 204. The top portion 211 and sidewalls create a work space that is variably constricted along the longitudinal axis for use of the model.

Figure 8:
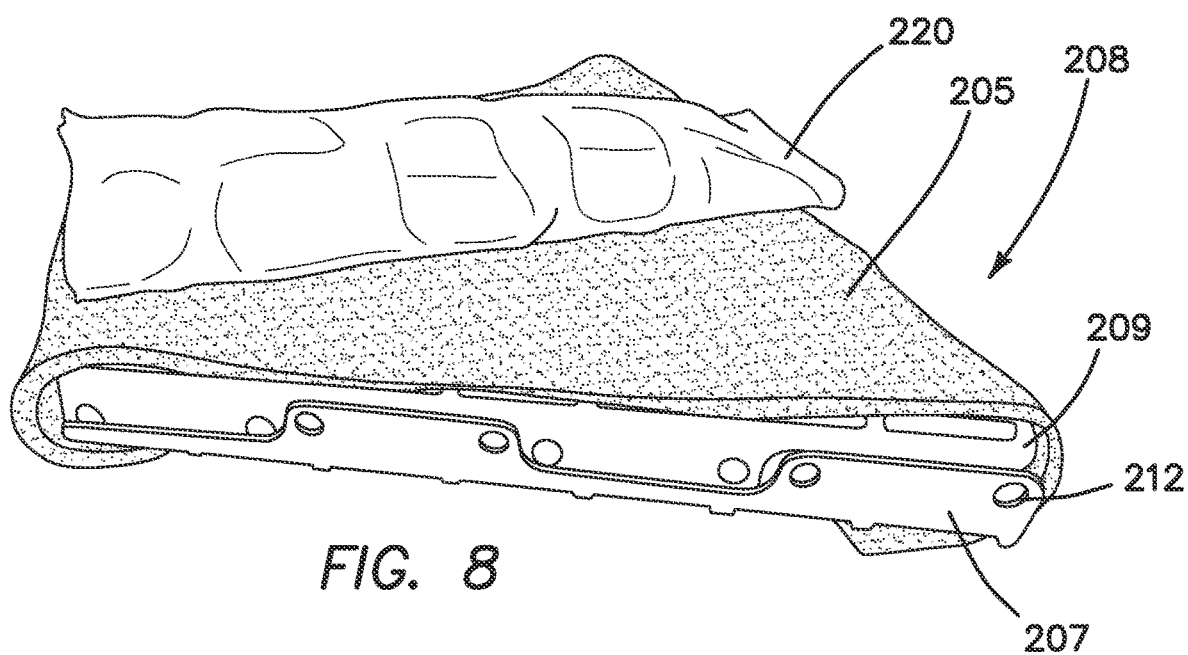
FIG. 8 is a side perspective view of a base of a frame according to various embodiments of the present invention.
Figure 9:
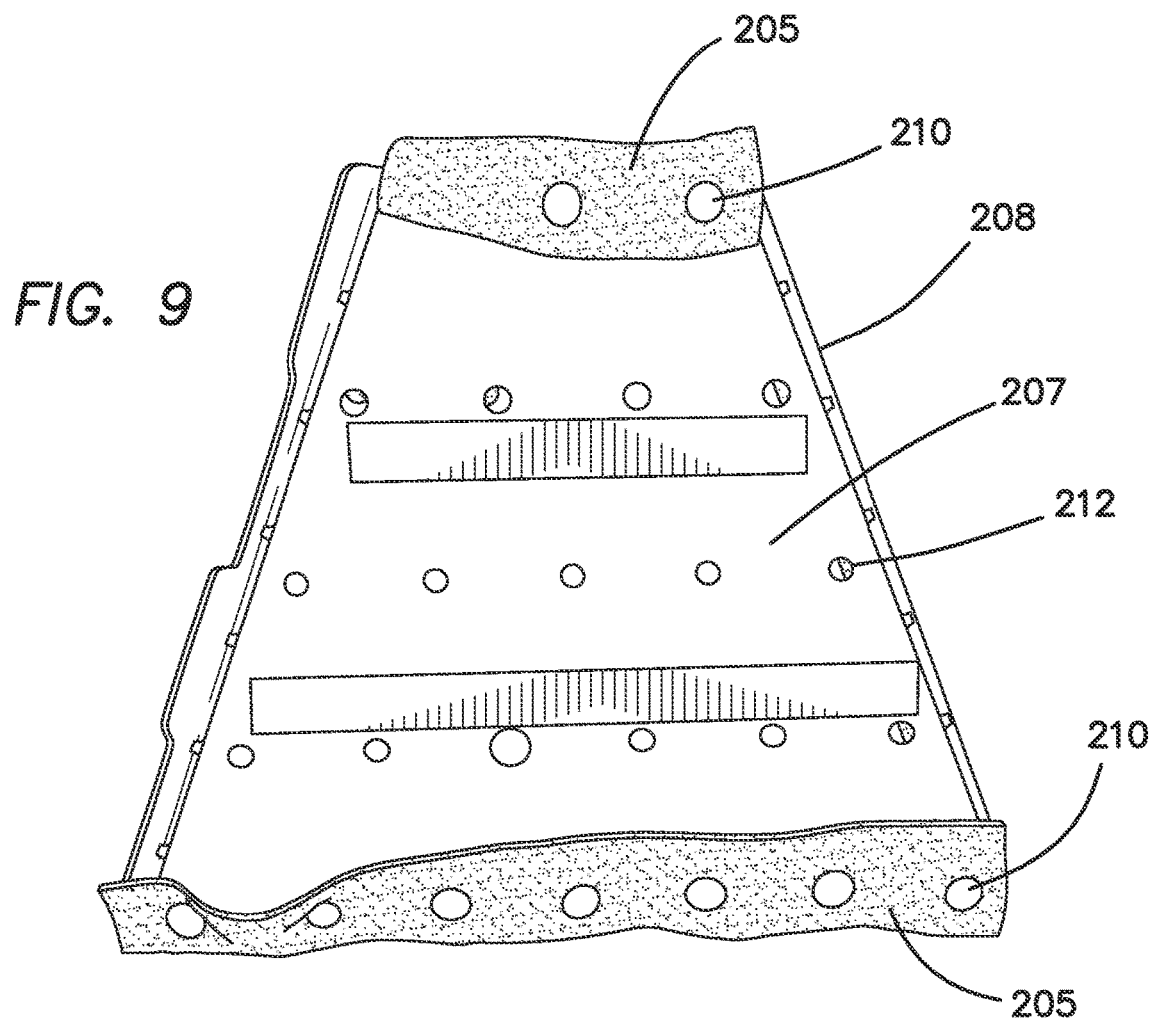
FIG. 9 is a bottom perspective view of a base of a frame according to various embodiments of the present invention.

With particular reference to FIGS. 8-9, the base portion is shown in greater detail. The base or bottom portion 208 includes one or more levels such as a second deck 209 located above a first deck 207. A silicone sheet 205 is fastened with fasteners 210. The fasteners 210 pierce the sheet 205 and snap into the apertures 212 in the base portion 208 of the frame 204. The silicone sheet 205 is employed to aid in the assembly of the model. Specifically, the silicone sheet 205 serves as a location for easy silicone-to-silicone attachment; wherein silicone-to-plastic attachment is more difficult to accomplish. Silicone adheres to silicone easily and removal of a silicone organ structure from the frame 204 is simplified with the silicone sheet 205 which can be unfastened and the model interchanged. The silicone sheet 205 is not an anatomically correct component of the human anatomy. Therefore, this model is not an accurate reproduction of human anatomy. Nevertheless, the appearance of the model maintains anatomical integrity for the user during procedural training employing laparoscopic techniques. The silicone sheet 205 creates a background for the user. This backdrop does not detract from the realism that is significant to user such as the simulated organs placed onto or attached to the backdrop of the silicone sheet 205. FIG. 8 illustrates a simulated colon 220 attached to the silicone sheet 205. The simulated colon in various embodiments being made of silicone or a material accommodating adherence to silicone or like material unlike plastic. In various embodiments, the simulated colon 220 is made of a second material, such as silicone, or at least a bottom portion thereof and sheet 205 is made of a first material. In various embodiments, the first material and second material are the same and/or are made of silicone. FIG. 9 illustrates the underside of the bottom portion 208 having two strips of fastener material such as a hook-and-loop type fastener for connecting the model to the base of a surgical trainer 10. In various embodiments, the first deck 207 and/or the second deck 209 are made of a third material, such as plastic, different from the first material, such as silicone.

Figure 10:
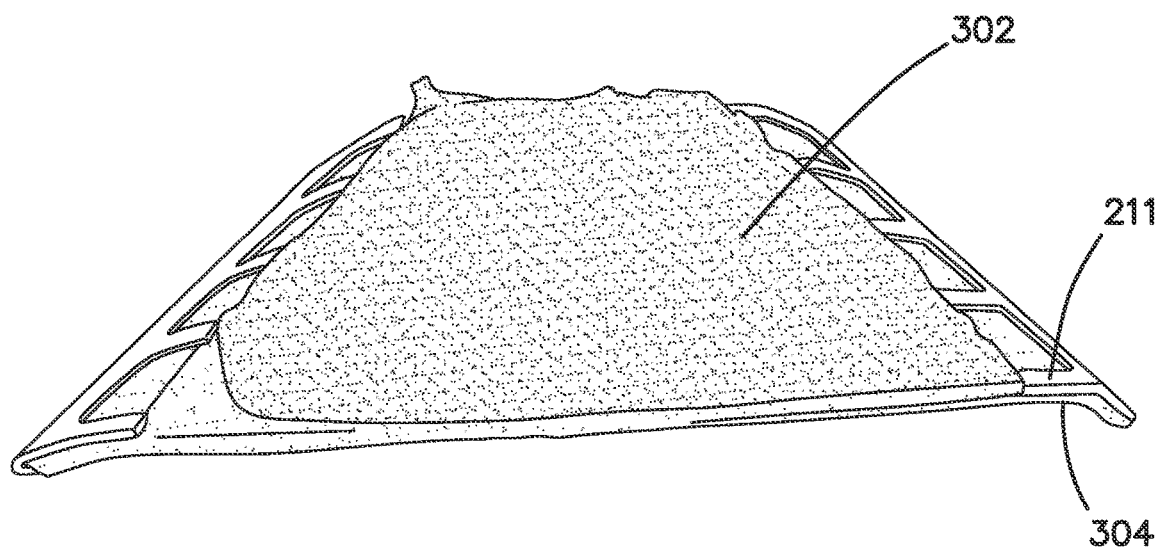
FIG. 10 is a top perspective view of a top portion or wall of a frame according to various embodiments of the present invention.
Figure 11:
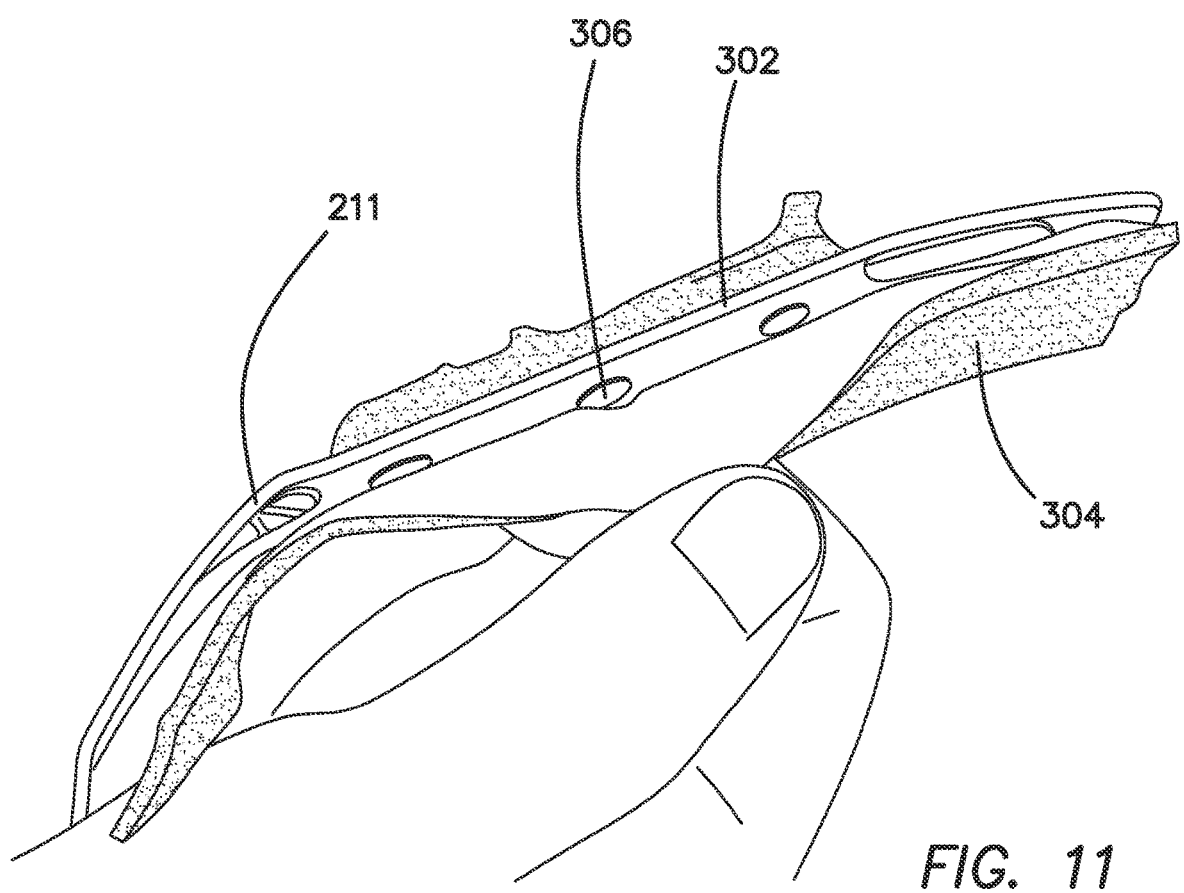
FIG. 11 is a side view of a top portion of a frame according to various embodiments of the present invention.
Figure 12:
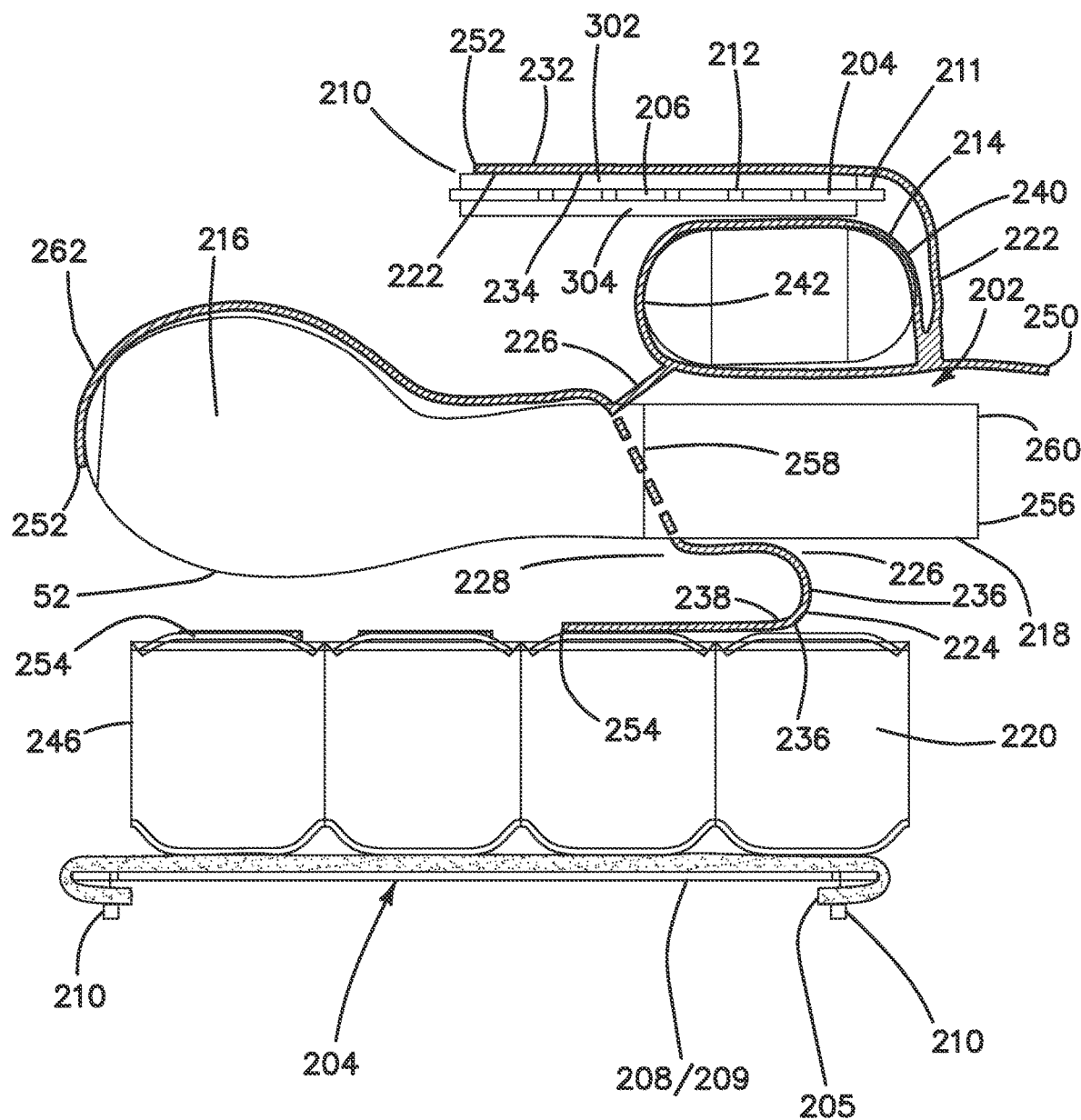
FIG. 12 is a side elevational schematic of a hysterectomy model according to various embodiments of the present invention.

With particular reference to FIGS. 10-12, in accordance with various embodiments, the upper wall or top portion 211 is removable from the sidewalls which allows placement of the silicone model on the base 208, 209 before attaching the top portion 211. Apertures in the top portion 211 are used to attach to the sidewalls with fasteners 210. Other apertures 212 are employed for silicone organ interface with the frame 204 and/or upper wall 211. The upper wall is made of a sixth material, such as rigid plastic, which in various embodiments is overlaid or covered with a layer made of a fourth material, such as silicone, that is different from the sixth material. In various embodiments, the upper wall is covered on an upper surface with a layer made of a fourth material, such as silicone, and covered on a bottom surface with a layer made of a fifth material that is the same as the fourth material, but that is different from the sixth material. In particular, the silicone layers 302, 304 cover the rigid plastic of the upper wall such that the two layers of silicone 302, 304 at points are directly connected to each other, e.g., through apertures in the upper wall, and sandwich the upper wall between the layers. In various embodiments, the top portion 211 is formed by curing a first layer of silicone 302, placing the top portion 211 having a plurality of apertures 212 formed therethrough onto the cured first layer 302 and then casting the second layer 304 onto the other side of the top portion 211 such that the uncured silicone, e.g., the second layer, passes through the apertures 212 and into contact with the first layer 302 of silicone, thereby, binding the first layer 302 and the second layer 304 together with the top portion 211 securely sandwiched between the two layers 302, 304 after the second layer 304 has cured. Fingers 306 of silicone passing through apertures 212 in the top portion 211 can be seen, for example, in FIG. 11. The second layer 304 is applied while uncured so as to interlock with the adjacent first layer 302 to embed the top portion 211. The top portion 211 imparts structural rigidity to the resulting frame 204. The two layers 302, 304 are attached in selective areas where apertures are formed 212 allowing for the application of an adjacent uncured silicone layer 302 through the holes of the top portion 211 for attachment to the adjacent layer 304 in select areas defined by the location of the apertures 212.

Turning now to FIG. 12 and with reference back to FIGS. 2-4, the plurality of simulated organ structures 202 and its connection to the frame 204 will now be described. The plurality of simulated organ structures 202 includes one or more of a simulated bladder 214, a simulated uterus 216, a simulated vaginal canal 218, a simulated rectum/colon 220, a first sheet 222, a second sheet 224, and a third sheet 226. The plurality of organ structures 202 are interconnected as shown in FIG. 12 and in turn connected to the frame 204. Tubular shaped vasculature, ducts, arteries 274 and the like in addition to other simulated organs structures not mentioned herein may be included in this model in an anatomically correct or anatomically similar arrangement for the same or different anatomical location of the body.

The simulated bladder 214 forms a closed receptacle with an outer membrane made of pink-colored silicone. The interior of the simulated bladder 214 may be filled with polyfil or other material to maintain its shape. The simulated bladder 214 has a proximal end 240 and a distal end 242. The simulated uterus 216 is also made of silicone. The simulated uterus 216 has a proximal end 260 and a distal end 262. The simulated vaginal canal 218 is a tubular structure made of silicone and may optionally contain an embedded mesh layer. The simulated vaginal canal 218 has a proximal end 256 and a distal end 258. The simulated rectum 220 is a tubular structure made of silicone with molded transverse folds. The simulated rectum 220 has a proximal end 244 and a distal end 246. Each of the first sheet 222 and the second sheet 224 comprises a large flat planar layer of silicone material. Both sheets 222, 224 represent the peritoneum. The first sheet 222 has a first surface 232 and a second surface 234 and a proximal end 248 and a distal end 250. The second sheet 224 has a first surface 236 and a second surface 238 and a proximal end 252 and a distal end 254.

With continued reference to FIG. 12, the assembly, configuration and connection of the plurality of simulated organ structures 202 will now be described. The distal end of the bladder 242 is attached to the first surface 232 of the first sheet 222 with adhesive such that the first sheet 222 wraps around the distal end 242 of the simulated bladder 214 from the bottom of the simulated bladder to the top of the simulated bladder 214. The second surface 234 is attached to the first silicone layer 302 near the distal end 248 of the first sheet 222 with adhesive. The first sheet 222 is folded in an approximate U-shape such that the distal end 250 of the first sheet 222 and, in particular, the second surface 234 of the first sheet 222, is attached to the simulated uterus 216 and attached to the simulated vaginal canal 218 via the dissecting layer 226 using adhesive. The first sheet 222 forms a pouch around the edge 242 of the bladder 214. The first sheet 222 is adhered to itself and wrapped around the top of the top portion 211 and adhered with glue to the first silicone layer 302.

The dissecting layer 226 is a construct comprising a silicone layer that may include a fiber layer. In such a variation, while the silicone dissecting layer 226 is uncured, a fiber layer is embedded to form the dissecting layer 226. The dissecting layer 226 is attached to the simulated vaginal canal 218. Although the dissecting layer 226 is shown with the same reference number, two dissecting layers 226 may be provided on either side of the simulated vaginal canal 218 as shown in the figures. The dissecting layer 226 may also be called a third sheet. Both sheets 222, 224 represent the peritoneum and the third sheet 226 represents a bladder flap or peritoneal reflection. Also, the dissecting layer 226 is attached to distal end 258 of the simulated vaginal canal 218. The dissecting layer 226 is a critical connection for the hysterectomy procedure. In one variation, the first sheet 222 is glued down to the simulated uterus 216 and, in another variation, the second sheet 224 is glued up to meet the bladder 214.

The second sheet 224 is attached between the simulated uterus 216 and the simulated rectum 220 as shown in FIG. 12. In particular, the first surface 236 at the distal end 252 of the second sheet 224 is attached near the distal end 262 of the simulated uterus 216. The second sheet 224 is attached along the length of the simulated uterus 216 toward the proximal end 260 using adhesive. The second sheet 224 is attached to the dissecting layer 226. In particular, the first surface 236 of the second sheet 224 is attached to the silicone layer 228 of the dissecting layer 226 using adhesive. The second sheet 224 includes a slit in order to pass the simulated uterus 216 through such that the second sheet 224 extends upwardly as shown with the dotted line. The second sheet 224 then extends proximally before turning distally such that the surface 236 is adhered to the simulated rectum 220. The simulated rectum 220, in turn, is adhered to silicone sheet 205. In various embodiments, tissue structures are connected to the base via adhesion to supportive structures. The apertures 212 on the frame 204 in various embodiments are used to create a mechanical connection between tissue structures and the base utilizing tissue sheets and silicone as a mechanical link through the apertures. The tissue sheets involved in this connection are not anatomically correct and are only used for structural and/or aesthetic purposes.

The plurality of the simulated organ structures 202 are connected to the frame 204 in a suspended manner. While suspended from the top frame 204, the interconnected plurality of simulated organ structures 202 advantageously pendulate and move together in a realistic fashion wherein the point of contact with instruments and the like will move most and simulated organs distal to the point of contact with instruments move to a lesser degree. The bottom side of the simulated rectum 220 is attached with adhesive to the silicone sheet 205 wrapped around the bottom portion 208 of the frame 204. Hence, the plurality of simulated organ structures is spanned across the central opening/lumen of the frame 202 with the first sheet 222, second sheet 224 and third sheet 226 forming an interconnecting webbing. The proximal end 260 of the simulated uterus 216 is inserted into the distal end 258 of the simulated vaginal canal 218 and joined together with adhesive. A simulated cervix is provided made of silicone and located inside the simulated uterus 216 at the proximal end 260.

Simulated organ structures are connected to the frame described above to provide suspension and support in an orientation which most closely replicates the human anatomy. Previously, organ structures were adhered directly to the frame with adhesives or fasteners. However, fasteners and adhesive may not provide a strong enough bond to prevent disassembly during use of the model. Placement of adhesive and fasteners in the model could also pose confusion to the user during use, due to the presence of a component which does not represent relevant anatomy. In order to maintain anatomical integrity, organ structures are connected to the base via supportive structures made of material that is the same or similar in appearance and functionality to the organ structure, such as silicone. Silicone adheres easily to silicone, thus creating an interface that allows organ structures made of silicone or the like to adhere directly to supportive structures made of silicone or a similar compatible adhesive yet functional and structural material creates a strong bond which can withstand forces applied to the organ structure during simulated procedural training. To implement this silicone-to-silicone adhesion, supportive structures such as the first silicone layer 302, second silicone layer 304 and the silicone sheet 205 can be adhered to the frame 204 with adhesive or fasteners which, when incorporated within the supportive structure and frame component, can be located under an organ structure or other frame component such that it does not cause any visual confusion or distraction for the user during procedural training. Hence, the supporting structures 302, 304, and 205 serve, not only, as an important visual backdrop, but also, as a strong way for connecting the simulated organs to a rigid plastic frame in a silicone-to-silicone attachment with or without adhesive. Simulated organ structures are then adhered to the supportive structure using silicone, silicone glue or adhesive. In another variation, supportive structures can embed a rigid or plastic frame component using silicone as an adhesive through apertures on the base creating a mechanical link between the silicone layers after the silicone is cured. The supportive structures are designed and placed in an orientation such that they appear to maintain anatomical integrity of the simulated organ structures. This prevents the supportive structures from causing visual confusion or distraction to the user during simulated procedural training. However, the supportive structures do not represent any anatomical structures necessary for realistic visualization of the procedural training. Hence, they serve a unique function melding unrealistic structural support layers 302, 304, 205 in an environment of realistic simulated organs. Simulated organ structures are then adhered to the supportive structure using silicone, silicone glue or adhesive. Previously, plastic frame components could cause confusion and/or distraction to the user during procedural training, for example, with a color and texture and hardness that can distract the user into mistakenly thinking that observation of bone, cartilage or the like is being made. Thus, the added supportive structures are also used to disguise the base components. The addition of supportive structures create both visual and functional improvements, minimizing the number of visible components that do not maintain the anatomical integrity of the model during use and improving the strength of organ structure adhesion to frame components. Although at least three supportive structures 302, 304 and 205 are described above, any number of supportive structures may be employed around the frame in a similar fashion in different locations such as on the sidewalls.

Figure 7:
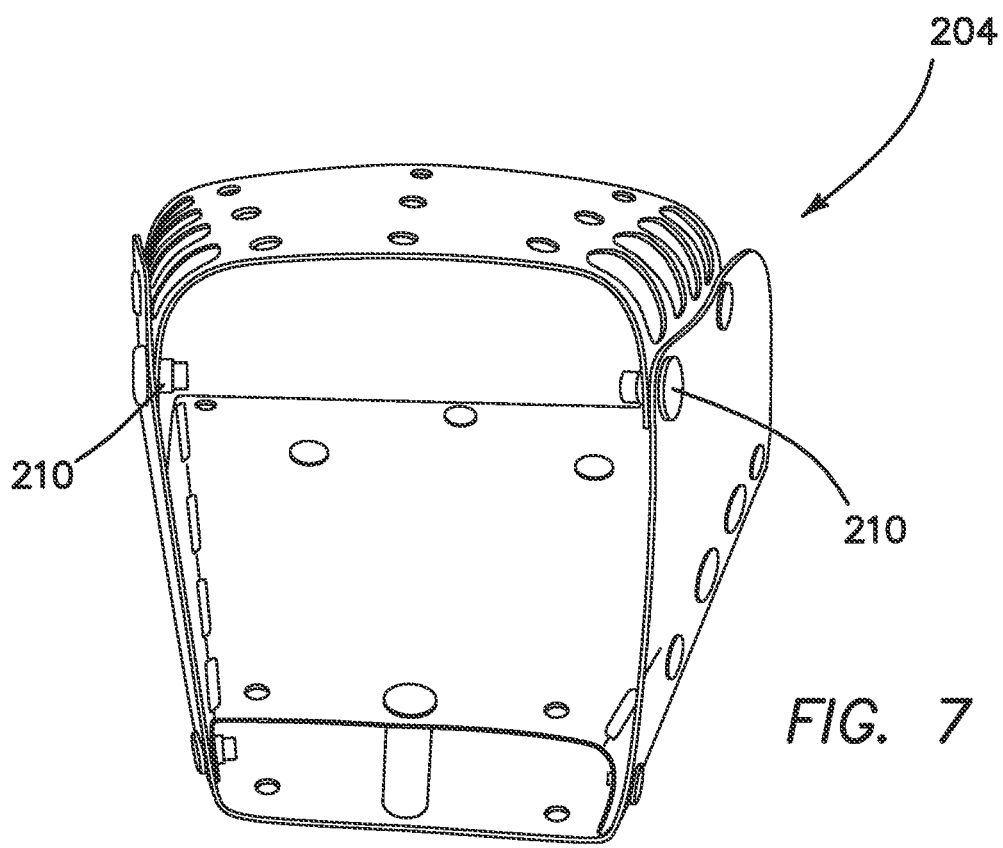
FIG. 7 a front perspective view of a frame according to various embodiments of the present invention.

Tubular shaped vasculature, ducts, arteries and the like 274 in addition to other simulated organs structures not mentioned herein may be included in this model in an anatomically correct or anatomically similar arrangement for the same or different anatomical location of the body. Upon attachment, simulated vasculature 274, ducts, fallopian tubes, ureters or other anatomical or non-anatomical structure having a tubular/cylindrical form and typically made of silicone are pulled through appropriately-sized apertures 212 as shown in FIGS. 7-8 to further support the connected simulated tissue structures and maintain them in their proper orientation/position. These tubular structures have a free end and another end that is attached to other simulated tissue structures. The free end is passed through an aperture 212 in the frame sidewall and can be secured with adjustable length to adjust the tension on the simulated tissue structures to which it is connected. For example, a loose tension may be created by securing the tubular structure with more slack between the frame and other simulated tissue structure. Alternatively, tension on the simulated tissue may be increased by pulling the tubular structure taunt with respect to the frame to create a relatively less pendulating simulated tissue construct within the frame. The tubular rope-like structure can be tied into a knot along its length to adjust the tension. The knot diameter is made larger than the aperture 212 in the frame in order to secure the larger tissue structure to the frame. The knots 275 may be untied to remove the simulated tissue structure or re-tied to provide a different tension level.

In various embodiments, the tubular rope-like structure is threaded through one or more apertures on the base and connected to itself forming a ring for additional strength. In various embodiments, the tubular silicone simulated vasculature 274, ducts, fallopian tubes, ureters or other anatomical or non-anatomical structure having a tubular/cylindrical form are provided with rivets at their distal end. The rivets include a distal end for connection with the frame and a proximal portion embedded or swaged into the ends of the silicone tubular structure to make a mechanical connection. The rivet-like fastener 210 serves as an interface connection between the soft, pliable silicone of the simulated tissue structures and the rigid plastic frame. The simulated tissue structures are often delicate and may tear easily if not reinforced. This makes it difficult to connect such artificial tissue structures to the frame.

Figure 3:
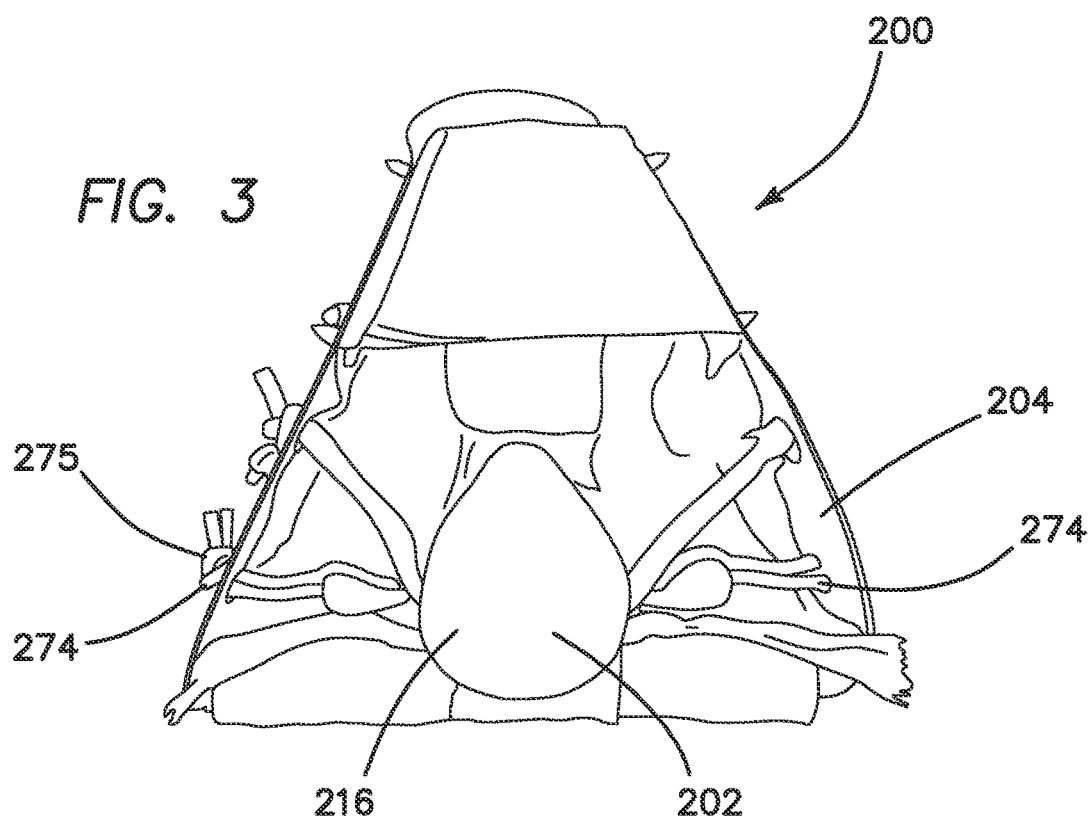
FIG. 3 is a top perspective view of a model according to various embodiments of the present invention.
Figure 4:
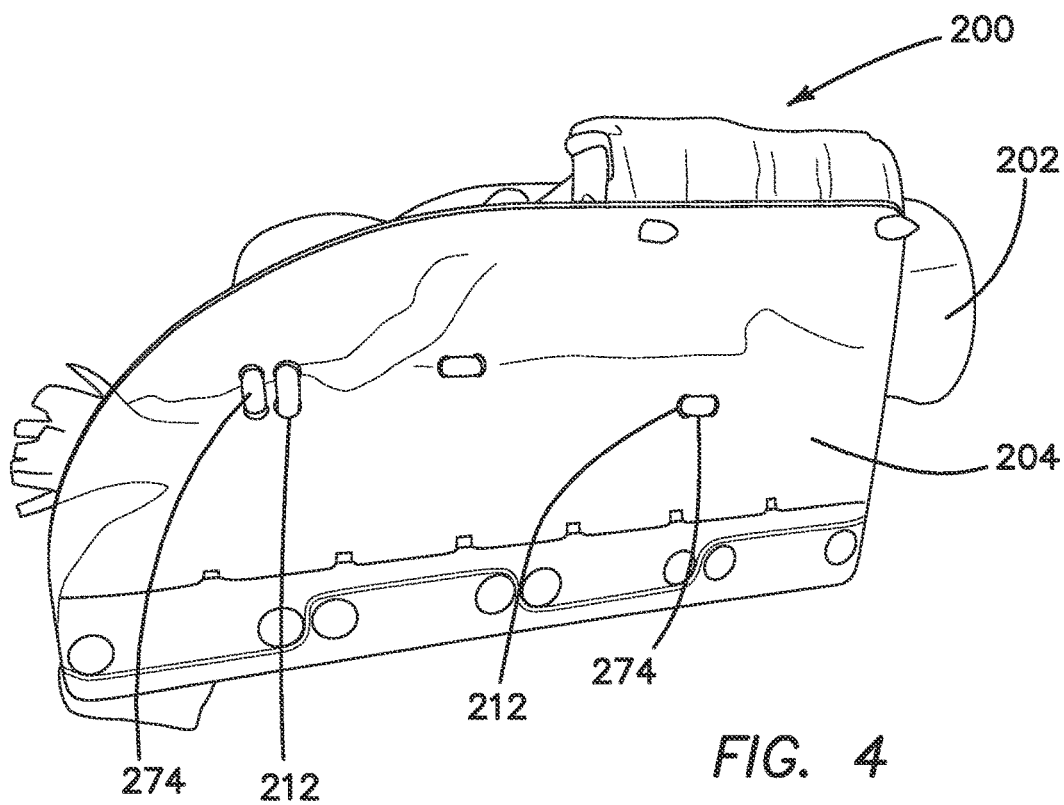
FIG. 4 is a side perspective view of a model according to various embodiments of the present invention.
Figure 5:
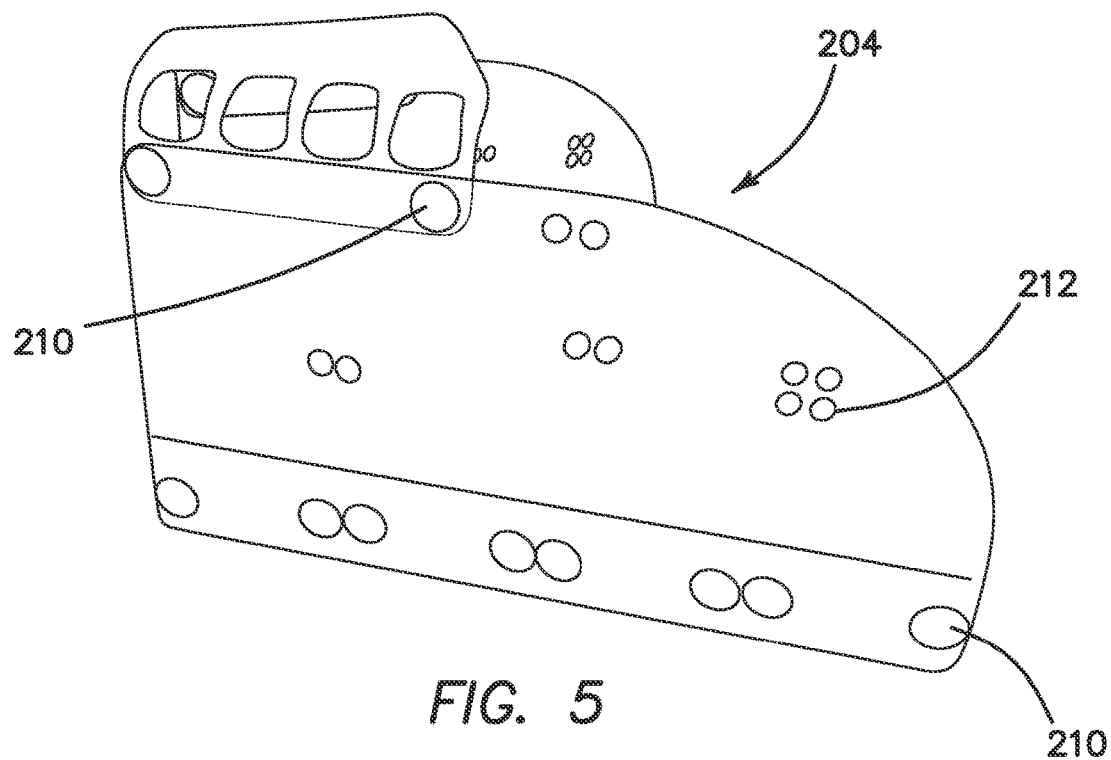
FIG. 5 is a side perspective view of a frame according to various embodiments of the present invention.

As can be seen in FIG. 3, the simulated vasculature 274 on the left side is passed through apertures 212 and fastened with knots 275 that are tied outside the frame 204 as described above. The simulated vasculature 274 on the right side is passed through two apertures 212 as will be described hereinbelow. The different methods of attachment shown in FIG. 3 are for illustrative purposes. Two apertures 212 are employed to fix the vasculature 274 because it was discovered that the silicone vessels can be severed during transport and/or friction arising between the rigid, sharp plastic frame and the soft silicone. Two side-by-side apertures 212 are formed in the frame 274. The simulated silicone vasculature 274 is passed through both holes and glued to itself thus forming a loop. Silicone, silicone glue and quick-dry adhesive can be used for attaching the vasculature 274. Using silicone is useful because the extra silicone provides a buffer which helps prevent the vasculature 274 from severing. The loop is clearly visible in FIG. 4 where the side-by-side apertures 212 are located above and below each other. The string-like vasculature 274 passes through one aperture 212, forming a U-shaped loop, and passes back into the lumen of the frame 204 through the adjacent aperture 212. Uncured silicone is applied as an adhesive and allowed to cure. The extra silicone further secures the vasculature 274 to the frame 204.

Simulated vessels 274 are strung through holes in the frame 204 to provide suspension of the silicone components in an orientation which most closely replicates the human anatomy. The simulated vessels are then tied off to fix them in the appropriate location and prevent shifting of the simulated tissue that is suspended. This method of fixation through the rough and sharp frame components can cause severing of the simulated vessels 274 during use and transport of the model which compromises the accurately simulated suspension of organ structures, thus hindering realistic procedural training for the user. To prevent severing of the vessels or shifting during transport while maintaining anatomical integrity, vessels 274 are strung through two apertures 212 and/or reinforced with silicone to create a ring or loop at each vessel/side wall junction. This method of loop fixation prevents unnecessary friction at the vessel/sidewall junction during use and transport preventing the severing of the vessels yet provides accurate suspension of the model. Furthermore, the reinforcement that loop fixation allows users to apply greater force to the simulated anatomy during procedural training without jeopardizing the structural integrity of the model.

In use, the model 200 is placed inside a laparoscopic trainer 10 and connected to the trainer 10 such as via a transvaginal adapter. The transvaginal adapter is formed as a leg configured to support the top cover 16 of the trainer 10. It is configured for simulating transvaginal surgery including transvaginal hysterectomies. The transvaginal adapter includes a flat plate having an inner surface for facing toward the interior of the trainer and an outer surface for facing outwardly towards the user. The plate has a rectangular shape and includes an aperture passing through the plate from the inner surface to the outer surface. In various embodiments, the aperture is circular in shape. In other various embodiments, the aperture is elongate elliptical, oval-like in shape and oriented vertically along the longitudinal axis of the adapter. In other various embodiments, the aperture is elongate elliptical, oval-like in shape and oriented perpendicularly to the longitudinal axis of the adapter. The transvaginal adapter is located between the top cover 16 and the base 18 and provides a side access aperture lateral to the trainer 10 or substantially perpendicular to the top cover 16 and the base 18. The access aperture is extra-large to simulate a pre-retracted vaginal canal as described above. The proximal end 256 of the simulated vaginal canal 218 is stretched over the access aperture to connect the simulated vaginal canal 218 to the adapter. The adapter in various embodiments secures the model to the trainer 10.

A user of the model may approach the simulated uterus 216 with surgical instruments and retractors through the transvaginal adapter to perform a transvaginal hysterectomy. Alternatively, the simulated uterus 216 may be approached through the simulated abdominal wall of the top cover 16 of the trainer 10. The user will practice laparoscopic surgical skills, employing a trocar and scope to examine the anatomy and perform the simulated surgical hysterectomy. The procedure involves making key incisions to detach the uterus and then remove it. In particular, the model 200 provides the first sheet 222, second sheet 224 and third sheet 226 and/or silicone webbing that make the incisions and separation of the simulated uterus 216 realistic. Also, the KEVLAR synthetic fiber mesh reinforced simulated cervix prevents tearing of the silicone when being pulled. The user may further practice suturing the simulated vaginal canal 218 after removal of the simulated uterus 216. For this purpose, the simulated vaginal canal 218 is provided with an embedded mesh that makes it possible for the silicone to hold sutures without easily tearing. After use, the model 200 is removed from the trainer 10 and the plurality of simulated organ structures 202 is removed from the model 200. A new plurality of simulated organ structures 202 is then connected to the frame 204 and inserted into the trainer 10 for continued practice.

Various portions in accordance with various embodiments of the model can be made of one or more organic base polymer including but not limited to hydrogel, single-polymer hydrogel, multi-polymer hydrogel, rubber, latex, nitrile, protein, gelatin, collagen, soy, non-organic base polymer such as thermo plastic elastomer, KRATON®, silicone, foam, silicone-based foam, urethane-based foam and ethylene vinyl acetate foam and the like. Into any base polymer one or more filler may be employed such as a fabric, woven or non-woven fiber, polyester, nylon, cotton and silk, conductive filler material such as graphite, platinum, silver, gold, copper, miscellaneous additives, gels, oil, cornstarch, glass, dolomite, carbonate mineral, alcohol, deadener, silicone oil, pigment, foam, poloxamer, collagen, gelatin and the like. The adhesives employed may include but are not limited to cyanoacrylate, silicone, epoxy, spray adhesive, rubber adhesive and the like.

The above description is provided to enable any person skilled in the art to make and use the present invention and perform the methods described herein and sets forth the best modes contemplated by the inventors of carrying out their inventions. Various modifications, however, will remain apparent to those skilled in the art. It is contemplated that these modifications are within the scope of the present disclosure. Different embodiments or aspects of such embodiments may be shown in various figures and described throughout the specification. However, it should be noted that although shown or described separately each embodiment and aspects thereof may be combined with one or more of the other embodiments and aspects thereof unless expressly stated otherwise. It is merely for easing readability of the specification that each combination is not expressly set forth.

Although the present invention has been described in certain specific aspects, many additional modifications and variations would be apparent to those skilled in the art. It is therefore to be understood that the present invention may be practiced otherwise than specifically described, including various changes in the size, shape and materials, without departing from the scope and spirit of the present invention. Thus, embodiments of the present invention should be considered in all respects as illustrative and not restrictive.

The invention claimed is:

1. A surgical simulator for surgical training comprising:
   a frame having a proximal end and a distal end, wherein a cross-sectional area of a lumen of the frame increases from the proximal end to the distal end; and
   at least one artificial tissue structure removably connected to and suspended within the frame;
   wherein at least a portion of the frame comprises a plurality of supportive structures that are connected to and located inside the frame to provide a silicone-to-silicone interface for the at least one artificial tissue structure.

2. The surgical simulator of claim 1, wherein one or more of the plurality of supportive structures are removable from the frame.

3. The surgical simulator of claim 1, wherein one or more of the plurality of supportive structures comprise at least two layers of silicone positioned on opposite sides of the portion of the frame and connected together through an aperture associated with that portion of the frame.

4. The surgical simulator of claim 3, wherein the at least two layers of silicone are cured onto the opposite sides of the portion of the frame.

5. The surgical simulator of claim 1, wherein the plurality of supportive structures are configured to maintain anatomical integrity for the frame simulating a pelvis.

6. The surgical simulator of claim 5, wherein the plurality of supportive structures are made of the same material as the at least one artificial tissue structure.

7. The surgical simulator of claim 6, wherein the at least one artificial tissue structure comprises a simulated uterus and bladder.

8. The surgical simulator of claim 1, wherein the frame is defined by:
   a first wall that defines a top planar surface,
   a second wall that is parallel with the first wall and that defines a bottom planar surface, and
   a third wall and a fourth wall that are both configured to interconnect the first wall and the second wall,
   wherein the first, second, third, and fourth walls define the lumen of the frame.

9. The surgical simulator of claim 8, wherein the plurality of supportive structures are associated with the second wall.

10. The surgical simulator of claim 8, wherein the first wall is removable from the rest of the frame to facilitate introducing the at least one artificial tissue structure into the frame.

11. The surgical simulator of claim 8, wherein the frame further comprises a raised level above the second wall, and wherein the at least one artificial tissue structure can be placed on one or both of the second wall or the raised level.

12. The surgical simulator of claim 1, wherein the at least one artificial structure is removably connected to and suspended within the frame via the plurality of supportive structures without the use of adhesives.

13. A surgical simulator for surgical training comprising:
   a plurality of walls removably connected to each other to form a frame having a lumen; and
   a plurality of supportive structures that are removably connected to one or more of the plurality of walls and located within the lumen, the plurality of supportive structures configured to provide a silicone-to-silicone interface,
   wherein the lumen of the frame is configured to receive at least one artificial tissue structure, and
   wherein the at least one artificial tissue structure is made of silicone and is configured to connect with the frame and be suspended within the lumen via the plurality of supportive structures.

14. The surgical simulator of claim 13, wherein the plurality of supportive structures comprise at least two layers of silicone positioned on opposite sides of at least one of the plurality of walls.

15. The surgical simulator of claim 14, wherein the at least two layers of silicone are cured onto the opposite sides of the at least one of the plurality of walls.

16. The surgical simulator of claim 14, wherein the plurality of supportive structures are configured to maintain anatomical integrity for the plurality of walls simulating a pelvis.

17. A surgical simulator for surgical training comprising:
   a plurality of walls removably connected to each other to form a frame having a lumen;
   an artificial tissue structure, the lumen of the frame configured to receive the artificial tissue structure;
   a first supportive structure connected to an inner surface of a first wall of the plurality of walls, the first supportive structure connected to a first portion of the artificial tissue structure through a first silicone-to-silicone interface; and
   a second supportive structure connected to an inner surface of a second wall of the plurality of walls, the second wall opposing the first wall and the second supportive structure being connected to a second portion of the artificial tissue structure through a second silicone-to-silicone interface.

18. The surgical simulator of claim 17 wherein the first supportive structure comprises a first silicone sheet, the first portion of the artificial tissue structure comprises at least one of a simulated uterus and a simulated bladder, the second supportive structure comprises a second silicone sheet, and the second portion of the artificial tissue structure comprises at least one of a simulated colon and a simulated rectum.

19. The surgical simulator of claim 17, wherein the first and second walls are made of a material different and more rigid than the first and second supportive structures and further comprising a third supportive structure connected to an outer surface of the first wall.

* * * * *